(12) United States Patent
Holliger et al.

(10) Patent No.: US 7,429,467 B2
(45) Date of Patent: Sep. 30, 2008

(54) EMULSION COMPOSITIONS

(75) Inventors: Phillip Holliger, Cambridge (GB); Farid Ghadessy, London (GB)

(73) Assignee: Medical Research Council, London (GB)

( * ) Notice: Subject to any disclaimer, the term of this patent is extended or adjusted under 35 U.S.C. 154(b) by 130 days.

(21) Appl. No.: 10/844,720

(22) Filed: May 13, 2004

(65) Prior Publication Data

US 2004/0253731 A1    Dec. 16, 2004

Related U.S. Application Data

(63) Continuation of application No. PCT/GB02/05216, filed on Nov. 18, 2002.

(30) Foreign Application Priority Data

Nov. 16, 2001 (GB) .................................. 0127564.3

(51) Int. Cl.
C12P 21/02 (2006.01)
(52) U.S. Cl. .................... 435/68.1; 435/193; 435/317.1
(58) Field of Classification Search .................. 435/5, 435/6, 320.1, 69.1; 536/23.1; 424/450
See application file for complete search history.

(56) References Cited

U.S. PATENT DOCUMENTS

| | | | |
|---|---|---|---|
| 4,801,529 A | 1/1989 | Perlman et al. | |
| 5,413,924 A | 5/1995 | Kosak et al. | |
| 5,503,851 A | 4/1996 | Mank et al. | |
| 5,516,635 A | 5/1996 | Ekins et al. | |
| 5,989,892 A | 11/1999 | Nishimaki et al. | |
| 6,023,540 A | 2/2000 | Walt et al. | |
| 6,184,012 B1 | 2/2001 | Neri et al. | |
| 6,258,858 B1 | 7/2001 | Nakajima et al. | |
| 6,266,459 B1 | 7/2001 | Walt et al. | |
| 6,310,354 B1 | 10/2001 | Hänninen et al. | |
| 6,489,103 B1 * | 12/2002 | Griffiths et al. | 435/6 |
| 6,808,882 B2 | 10/2004 | Griffiths et al. | |
| 2001/0020011 A1 | 9/2001 | Mathiowitz et al. | |
| 2002/0022038 A1 * | 2/2002 | Biatry et al. | 424/401 |
| 2002/0119459 A1 | 8/2002 | Griffiths | |
| 2002/0155080 A1 * | 10/2002 | Glenn et al. | 424/70.5 |
| 2003/0124586 A1 | 7/2003 | Griffiths et al. | |
| 2004/0005594 A1 | 1/2004 | Holliger et al. | |
| 2004/0253731 A1 | 12/2004 | Holliger et al. | |
| 2005/0037392 A1 | 2/2005 | Griffiths et al. | |
| 2005/0042648 A1 | 2/2005 | Griffiths et al. | |
| 2005/0069920 A1 | 3/2005 | Griffiths et al. | |
| 2005/0079510 A1 | 4/2005 | Berka et al. | |
| 2005/0164239 A1 | 7/2005 | Griffiths et al. | |

FOREIGN PATENT DOCUMENTS

| | | |
|---|---|---|
| DK | 19646372 C1 | 6/1997 |
| EP | 0 579 347 B1 | 1/1994 |
| EP | 0579347 | 1/1994 |
| EP | 1482036 A2 | 12/2004 |
| WO | WO-91/05058 | 4/1991 |
| WO | WO-93/03151 | 2/1993 |
| WO | WO-93/03151 A | 2/1993 |
| WO | WO-93/08278 | 4/1993 |
| WO | WO-94/16332 | 7/1994 |
| WO | WO-94/23738 | 10/1994 |
| WO | WO 94/23738 | 10/1994 |
| WO | WO-94/24314 | 10/1994 |
| WO | WO-94/26766 | 11/1994 |
| WO | WO-95/11922 | 5/1995 |
| WO | WO-95/24929 | 9/1995 |
| WO | WO 95/24929 | 9/1995 |
| WO | WO-96/34112 A | 10/1996 |
| WO | WO-96/40723 | 12/1996 |
| WO | WO-97/40141 | 10/1997 |
| WO | WO-97/47763 | 12/1997 |
| WO | WO-98/13502 | 4/1998 |
| WO | WO-98/23733 | 6/1998 |
| WO | WO-98/31700 A | 7/1998 |
| WO | WO-98/34120 | 8/1998 |
| WO | WO-98/37186 | 8/1998 |
| WO | WO-98/41869 A | 9/1998 |
| WO | WO 99/02671 | 1/1999 |
| WO | WO-99/02671 | 1/1999 |
| WO | WO99/25738 | 5/1999 |
| WO | WO-00/04139 | 1/2000 |
| WO | WO-00/40712 | 7/2000 |
| WO | WO-01/18244 | 3/2001 |
| WO | WO-02/22869 | 3/2002 |
| WO | WO-03/044187 | 5/2002 |

(Continued)

OTHER PUBLICATIONS

Tawfik et al. (Nature Biotechnology 1998; 16:652-656).*
Gäsperlin et al. (International J Pharmaceutics 2000, 196:37-50).*
Hsu et al (J Drug Targeting 1999, 7(4): 313-323).*
Jermutus et al. (Current Biology 1998; 9:534-548).*
Stiege et al. (J. Biotechnology; 41:81-90), 1995.*
Ghadessy, et al.; "Directed evolution of polymerase function by compartmentalized self-replication"; (2001); *PNAS;* 98: 4552-4557.
Tawfik and Griffiths; "Man-made cell-like compartments for molecular evolution"; (1998); *Nature Biotech.;* 16: 652-656.
European Patent Office Examination Report, Application No. 0277590.0-2107, Sep. 14, 2005.
Anarbaev et al., "Klenow fragment and DNA polymerase alpha-primase from serva calf thymus in water-in-oil emulsions", Biochimica et Biophysica Acta, 1998, pp. 315-324.

(Continued)

*Primary Examiner*—James Ketter
(74) *Attorney, Agent, or Firm*—Edwards Angell Palmer & Dodge LLP; Kathleen Williams; Jeffrey Kopacz

(57) ABSTRACT

An emulsion is useful in allowing a wide variety of gene products to be expressed via eukaryotic in vitro expression. The emulsion comprises a silicone based surfactant, a hydrophobic phase and a hydrophilic phase; wherein the hydrophilic phase comprises a plurality of compartments containing a functional in vitro eukaryotic expression system.

15 Claims, 3 Drawing Sheets

FOREIGN PATENT DOCUMENTS

| WO | WO-02/103363 | 12/2002 |
|----|--------------|---------|
| WO | WO-2004/069849 A2 | 8/2004 |
| WO | WO-2004/083443 A1 | 9/2004 |

OTHER PUBLICATIONS

Tawfik et al., "Man-made cell-like compartments for molecular evolution", Nature Biotechnology, Jul. 1998, vol. 16, pp. 652-656.

Chiou et al. (2001) "A Closed-Cycle Capillary Polymerase Chain Reaction Machine", Analytical Chemistry, American Chemical Society, 73:2018-2021.

Katsura et al. (2001) "Indirect Micromanipulation of Single Molecules in Water-In-Oil Emulsion", Electrophoresis, 22:289-293.

Kawakatsu et al. (1997), "Regular-Sized Cell Creation in Microchannel Emulsification by Visual Microprocessing Method", Journal of the American Oil Chemists' Society, 74:317-321.

Kopp et al. (1998). "Chemical Amplification: Continuous Flow PCR on a Chip", Science, American Association for the Advancement of Science, 280:1046-1048.

Lund, et al. (1998). "Assesment of Methods for Covalent Binding of Nucleic Acids to Magnetic Beads, Dynabeads, and the Characteristics of the Bound Nucleic Acids in Hybridization Reactions", Nucleic Acids Research, Oxford University Press, 16, No. 22, 20 pgs.

Lundeberg et al. (1995). "Solid-Phase Technology: Magnetic Beads to Improve Nucleic Acid Detection and Analysis", Biotechnology Annual Review, 1:373-401.

Nakano, et al. (2003). "Single-Molecule PCR Using Water-In-Oil Emulsion", Journal of Biotechnology, 102: 117-124.

Nakano et al. (1994) "High Speed Polymerase Chain Reaction in Constant Flow", Bioscience Biotechnology and Biochemistry, 58:349-352.

Park et al. (2003). "Cyndrical Compact Thermal-Cycling Device for Continuous-Flow Polymerase Chain Reaction", Analytical Chemistry, American Chemical Society, 75:6029-6033.

Russom et al. (2003). "Single-Nucleotide Polymorphism Analysis by Allele-Specific Extension of Fluorescently Labeled Nucleotides in a Microfluidic Flow-Through Device", Electrophoresis, 24:158-161.

Schneegass et al. (2001). "Miniaturized Flow-Through PCR With Different Template Types in a Silicone Chip Thermocycler", Lab on a Chip, Royal Society of Chemistry. 1:42-49.

Anarbaev, et al. (1998) Klenow Fragment and DNA Polymerase a-primase Fromserva Calf Thymus in Water-in-Oil Microemulsions, Biochimica et Biophysica Acta, 1384:315-324.

Atwell et al. (1999), Selection for Improved Subtilitases by Phage Display, Proc. Natl. Acad. Sci. USA, 96: 9497-9502.

Bas et al. (1990); Hormone Phage: An Enrichment Method for Variant Proteins with Aletered Binding Properties. PROTEINS: Structure, Function, and Genrtics, 8:: 309-314.

Bauer, Johann (1999); Advances in Cell Separation: Recent Developments in Couterflow Centrifugal Elutriation and Continuous Flow Cell Separation; J. Chiromotography 722:55-69.

Brody & Quake (1999) A sSelf-Assembled Microlensing Rotational Probe; Applied Physics Lettes 74: 144-146.

Chakrabarti, et al. (1994) Production of RNA by a Polymerase Protein Encapsulated Within Phospholipid Vesicles J. Mol. Evol. 39-555-559.

Chapman et al. (1994) In vitro Selection of Cataltic RNAs. Structural Biology 4:618-622.

Clarkson et al. (1994) In vitro Selection from Protein and Peptide Libraries; Trends in Biotechnology; 12:173-184.

Cull et al. (1992). Screening for Receptor Ligands Using Large Libraries of Peptides Linked to the C Terminus of the Iac Repressor. Proc. Natl. Accad. Sci. USA, 89: 1865-1869.

Demartis et al. (1999). A Strategy for the Isolation of Catalytic Activities from Repertoires of Enxymes Displayed on Phage. Academic Press Limited, Article No. jmbi, 1998, 2476, pp. 617-633.

Dressman et al. (2003). Transforming Single DNA Molecules into Fluorescent Magnetic Particles for Detection and Enumeration of Genetic Variations. PNAS 100: 8817-8822.

Eigen (1976). Wie Entsteht Information? Principien de Selbstoganisation in der Biologie, Berichte der Bunsen-Gesellschaft Fur Physikalische Chemi, 80(11); 1059-1081.

Eigen et al. (1980). Hypercycles and Compartments. Compartments Assists-but do not replace-Hypercyclic Organization of Early Genetic Information, J. Theor. Biol., 85: 407-411.

Eigen et al. (1991), The Hypercycle, Coupling of RNA and Protein Biosynthesis in the Infection Cycle of an RNA Bacteriophage, Biochemistry, 30(46): 11005-11018.

Ellington et al. (1990), In vitro Selection of RNA Molecules that Bind Specific Ligands, Nature, 346: 818-822.

Gold et al. (1995), divesity of Oligonucleotide Functions, Annu. Rev. Biochem., 64: 763-797.

Green et al. (1992), Selection of a Ribozyme that Functions as a Superior Template in a Self-Copying Reaction, Science, 258: 1910-1915.

Griffths & Tawfik (2003), Directed Evolution of an Extremely Fast Phosphotriesterase by in vitro Compartmentalization, Embo J. 22: 24-35.

Hanes et al. (1997), In vitro Selection and Evolution of Functional Proteins by Using Ribosome Display, PNAS 94: 4937-4942.

Jada, et al. (1997), Chemical Selection for Catalysis in Combinatorial Antobody Libraries, www.sciencenmag.org, 275: 945-948.

Jestin et al. (1999), A Method for the Selection of Catalytic Activity Using Phage Display and Proximity Coupling, Angew Chem. Int. 38: 1124-1127, No. 8.

Joyce et al. (1994), In vitro Evolution of Nucleic Acids, Structural Biology, 4: 331-336.

Keji et al., (1991), High-Sped Photodamage Cell Sorting: An Evaluation of the ZAPPER Prototype, Methods in Cell Biollogy, 42: 341-386.

Mattheakis et al. (1994), An in vitro Polysome Display System for identifying Ligands from Very Large Peptide Libraries, Proc. Natl. Acad. Sci. USA, 91: 9022-9026.

McCafferty et al. (1990), Phage Antibodies: Filamentous Phage Display Antibody Variable Domains, Nature, 348: 552-554.

Moore (1995), Exploration by Lamp Light, Nature, 374: 766-767.

Nemoto et al., (1997), In vitro Virus: Bonding of mRNA bearing Puromycin at the 3'-Teminal End to the C-Terminal End of its Encoded Protein on the Ribosome in vitrom, Federation of European Biochemical Societies, pp. 405-408.

Oberholzer et al., (1995), Enzymatic RNA Replication in Self-Reproducing Vesicles: An Approach to a Minimal Cell, Biochemical and Biophysical Research Communications, Academic Press, Inc., 207: 250-257.

Oberholzer et al. (1995), Polymerase Chain Reaction in Liposomes; Chemistry & Biology, 2: 677-682.

Pedersden et al. (1998), A Method for Directed Evolution and Functional Cloning of Enzymes, Proc. Natl. Acad. Sci. USA 95: 10523-10528.

Pelletier et al. (1999), An in vivo Library-versus Library Selection of Optimized Protein-Protein Interactions, Nature Biotechnology, 17: 683-690.

Roberts et al. (1997), RNA-Peptide Fusions for the in vitro Selection of Peptides and Proteins, Proc. Natl. Acad. Sci. USA 94: 12297-12302.

Sepp et al. (2002), Microbead Display by in virto Compartmentalisation: Selection for Binding Using Flow Cytometry, FEBS Letters, 532: 455-458.

Smith (1985), Filamentours Fusion Phage: Novel Expression Vectors that Display Cloned Antigens on the Virion Surface, Science, 228: 1315-1317.

Soumillion (1994), Selection of β-Lactamase on Filamentous Bacteriophage by Catalytic Activity, J. Mol. Biol., 237: 415-422.

Suzuki et al. (1996), Random Mutagenesis of Thermus Aquaticus DNA Polymerase I: Concordance of Immutable Sites in vivo with the Crystal Structure, Proc. Natl. Acad. Sci. USA, 93: 9670-9675.

Tawfik & Griffiths (1998), Man-Made Cell-Like Compartments for Molecular Evolution, Nature Biotechnology, 16: 652-656.

Tawfik et al. (1997), Effcient and Selective p-Nitrophenyl-Ester-Hydrolyzing Antibodies Elicited by a p-Nitrobenzyl Phosphonate Hapten, European Journal of Biochemistry, 244: 619-626.

Turek et al. (1990), Systematic Evolution of Ligands by Exponetial Enrichment: RNA Ligands to Bacteriophage T4 DNA Polymerase, Science, 249: 505-510.

Vainshtein et al. (1996) Peptide Rescue of an N-Terminal Truncation of the Stoffel Fragment of Tag DNA Polymerase, Protein Science, 5: 1785-1792.

Vogelsgtein et al. (1999), Digital PCR, Proc. Natl. Acad. Sci. USA, 96: 9236-9241.

Walde et al. (1994), Oparin's Reactions Revisted: Enzymatic Synthesis of Poly(adenylic acid) in Micelles and Self-Reproducing Vesicles, J. American Chemical Society, 116: 754-7547.

Warburton (1993), Microcapsules from Multiple Emulsions, royal Society of Chemistry, 138: 35-51.

Wick (1996), Enzyme-Containing Liposomes Can Endogenously Produce Membrane-Constituting Lipids, Chemistry & Biology, 3: 277-285.

Widersten et al. (1995), Glutathuione Transferases with Novel Active Sites Isolated by Phage Display from a Library of Random mutants, J. Mol. Biol. 250: 115-122.

Gasperlin et al.; Int'l J. Pharm. 2000; 196: 37-50.

Gasperlin et al., Int'l J. Pharm. 1994; 107: 51-56.

Ghadessy et al.; PNAS, 2001, 98: 4552-57.

Hsu et al. J. Drug Target, 1999: 7: 313-23.

International Search Report dated Mar. 19, 2003 (PCT GB02/05216).

* cited by examiner

1 2 3 4 5 6

EMULSION COMPOSITIONS

This application is a continuation of PCT/GB02/05216, filed Nov. 18, 2002, which claimed the priority of Great Britain application GB 0127564.3, filed Nov. 16, 2001, the entireties of which are hereby incorporated by reference.

FIELD OF THE INVENTION

The present invention relates, inter alia, to emulsions suitable for compartinentalisation of transcription/translation reactions and methods using such emulsions. In particular, the emulsions are useful for compartinentalisation of in vitro eukaryotic transcription/translation reactions.

BACKGROUND TO THE INVENTION

Compartmentalisation methods based on water-in-oil emulsions have recently been developed for use in repertoire selection methods (Tawfik & Griffiths 1998, Ghadessy et al 2001). Compartmentalisation segregates individual genes and their encoded products (delivered either via cells (Ghadessy et al, 2001) or expressed in situ (Tawfik & Griffiths, 1998)) into discrete, physically separate aqueous compartments, thus ensuring the linkage of genotype and phenotype during the selection process.

WO99/02671 (which is incorporated herein by reference) describes a method for isolating one or more genetic elements encoding a gene product having a desired activity. Genetic elements are first compartmentalised into microcapsules, which are preferably formed by emulsification, and are then transcribed and/or translated to produce their respective gene products (RNA or protein) within the microcapsules. Alternatively, the genetic elements may be contained within microcapsules of the emulsion and transcription and/or translation (expression) of the gene product can take place within using the cellular machinery. Genetic elements that produce a gene product having a desired activity can be subsequently sorted. For example, in some cases sorting may be due to the desired activity inducing a change in the microcapsule. In other cases sorting may be due to the desired activity inducing a change in the genetic element.

The method disclosed in WO99/02671 works well with bacteria. Although the cellular subcompartmentalisation approach could in principle be extended to include eukaryotic cells, e.g. yeast, insect or mammalian cells, for some applications it would be desirable to provide in situ expression directly in microcapsules using an in vitro eukaryotic transcription/translation system.

Previous successful expression of a prokaryotic enzyme, Hae methylase, has been reported using bacterial S30 extracts in emulsion (Tawfik D. & Griffiths A. D. 1998). However, such methods are not suitable for some proteins of interest, for example large multi-domain proteins and ribonucleoproteins which frequently cannot be expressed in functional form using bacterial extracts.

Thus it can be seen that a method which enables in situ expression directly in microcapsules using an in vitro eukaryotic transcription/translation system would provide a contribution to the art.

SUMMARY OF THE INVENTION

Accordingly, in a first aspect of the present invention, there is provided an emulsion comprising a surfactant, a hydrophobic phase and a hydrophilic phase comprising a plurality of microcapsules containing a functional in vitro eukaryotic expression system, wherein the surfactant is a chemically inert silicone-based surfactant.

In developing such a method, the present inventors have encountered repeated problems in maintaining efficient transcriptional/translational ability of an eukaryotic system, in particular the rabbit reticulocyte lysate system, when in emulsion. As described below, a number of modifications to emulsion compositions used with prokaryotic expression systems were unsuccessful in conferring such ability. However, it was surprisingly found that, when chemically inert silicone-based surfactants were employed in the emulsion composition, the efficiency of transcription of the eukaryotic transcription/translation system was markedly improved.

The emulsion allows the linkage of genotype and phenotype due to compartmentalisation of the eukaryotic expression system, whilst avoiding many of the disadvantages of cell-based systems. Thus, for example, it allows gene products to be obtained without the need for extraction or secretion from cells.

Accordingly, in a second aspect of the invention, there is provided a method of isolating one or more genetic elements encoding a gene product having a desired activity, comprising the steps of:
  (a) compartmentalising the genetic elements into microcapsules formed from an emulsion of the invention
  (b) expressing the genetic elements to produce their respective gene products within the microcapsules;
  (c) sorting the genetic elements which produce gene product(s) having the desired activity.

In a third aspect, the invention provides a method for preparing a gene product, comprising the steps of
  (a) preparing a genetic element encoding the gene product;
  (b) compartmentalising genetic elements into microcapsules formed from an emulsion of the invention;
  (c) expressing the genetic elements to produce their respective gene products within the microcapsules;
  (d) sorting the genetic elements which produce the gene product(s) having the desired activity; and
  (e) expressing the gene product having the desired activity.

In accordance with this aspect of the invention, step (a) preferably comprises preparing a repertoire of genetic elements, wherein each genetic element encodes a potentially differing gene product. Repertoires may be generated by conventional techniques, such as those employed for the generation of libraries intended for selection by methods such as phage display. Gene products having the desired activity may be selected from the repertoire, according to the present invention.

A fourth aspect of the invention provides a product selected using the method of the second aspect of the invention or prepared according to the third aspect of the invention. As used in this context, a "product" may refer to a gene product selected or prepared according to these aspects, or the genetic element (or genetic information comprised therein).

In a fifth aspect, the invention provides a method for screening a compound or compounds capable of modulating the activity of a gene product, comprising the steps of:
  (a) preparing a repertoire of genetic elements encoding gene product;
  (b) compartmentalising the genetic elements into microcapsules formed from an emulsion of the invention;
  (c) expressing the genetic elements to produce their respective gene products within the microcapsules;
  (d) sorting the genetic elements which produce the gene product(s) having the desired activity; and (e) contacting a gene product having the desired activity with the compound or compounds and monitoring the modulation of an activity of the gene product by the compound or compounds.

In the context of the present invention, a surfactant is considered to be "chemically inert" if it is substantially free of oxidating species, such as peroxides and aldehydes, and protein denaturing species. Surfactants having 40%, preferably 50%, more preferably 60%, 70%, 80%, 90%, 95%, or 98% less oxidating species and protein denaturing species than either one of conventional sorbitan monooleate (Span™80; ICI) and polyoxyethylenesorbitan monooleate (Tween™ 80; ICI) emulsifiers are considered to be "substantially free" of oxidating species and denaturing species.

The terms "isolating", "sorting" and "selecting", as well as variations thereof, are used herein. Isolation, according to the present invention, refers to the process of separating an entity from a heterogeneous population, for example a mixture, such that it is free of at least one substance with which it was associated before the isolation process. In a preferred embodiment, isolation refers to purification of an entity essentially to homogeneity. Sorting of an entity refers to the process of preferentially isolating desired entities over undesired entities. In as far as this relates to isolation of the desired entities, the terms "isolating" and "sorting" are equivalent. The method of the present invention permits the sorting of desired genetic elements from pools (libraries or repertoires) of genetic elements which contain the desired genetic element. Selecting is used to refer to the process (including the sorting process) of isolating an entity according to a particular property thereof.

In preferred embodiments of the methods of the invention, the sorting of genetic elements may be performed in one of essentially four techniques, details of which are given in WO99/02671.

(I) In a first embodiment, the microcapsules are sorted according to an activity of the gene product or a derivative thereof which makes the microcapsule detectable as a whole. Accordingly, the invention provides a method according to the second aspect of the invention wherein a gene product with the desired activity induces a change in the microcapsule, or a modification of one or more molecules within the microcapsule, which enables the microcapsule containing the gene product and the genetic element encoding it to be sorted. In this embodiment, therefore, the microcapsules are physically sorted from each other according to the activity of the gene product(s) expressed from the genetic element(s) contained therein, which makes it possible selectively to enrich for microcapsules containing gene products of the desired activity.

(II) In a second embodiment, the genetic elements are sorted following pooling of the microcapsules into one or more common compartments. In this embodiment, a gene product having the desired activity modifies the genetic element which encoded it (and which resides in the same microcapsule) in such a way as to make it selectable in a subsequent step. The reactions are stopped and the microcapsules are then broken so that all the contents of the individual microcapsules are pooled. Selection for the modified genetic elements enables enrichment of the genetic elements encoding the gene product(s) having the desired activity. Accordingly, the invention provides a method according to the second aspect of the invention, wherein in step (b) the gene product having the desired activity modifies the genetic element encoding it to enable the isolation of the genetic element. It is to be understood, of course, that modification may be direct, in that it is caused by the direct action of the gene product on the genetic element, or indirect, in which a series of reactions, one or more of which involve the gene product having the desired activity, leads to modification of the genetic element.

(III) In a third embodiment, the genetic elements are sorted following pooling of the microcapsules into one or more common compartments. In this embodiment, a gene with a desired activity induces a change in the microcapsule containing the gene product and the genetic element encoding it. This change, when detected, triggers the modification of the gene within the microcapsule. The reactions are stopped and the microcapsules are then broken so that all the contents of the individual microcapsules are pooled. Selection for the modified genetic elements enables enrichment of the genetic elements encoding the gene product(s) having the desired activity. Accordingly the invention provides a method according to the second aspect of the invention, where in step (b) the gene product having the desired activity induces a change in the microcapsule which is detected and triggers the modification of the genetic element within the microcapsule so as to allow its isolation. It is to be understood that the detected change in the microcapsule may be caused by the direct action of the gene product, or indirect action, in which a series of reactions, one or more of which involve the gene product having the desired activity leads to the detected change.

(IV) In a fourth embodiment, the genetic elements may be sorted by a multi-step procedure, which involves at least two steps, for example, in order to allow the exposure of the genetic elements to conditions which permit at least two separate reactions to occur. As will be apparent to a persons skilled in the art, the first microencapsulation step of the invention must result in conditions which permit the expression of the genetic elements—be it transcription, transcription and/or translation, replication or the like. Under these conditions, it may not be possible to select for a particular gene product activity, for example because the gene product may not be active under these conditions, or because the expression system contains an interfering activity. The invention therefore provides a method according to the second aspect of the present invention, wherein step (b) comprises expressing the genetic elements to produce their respective gene products within the microcapsules, linking the gene products to the genetic elements encoding them and isolating the complexes thereby formed. This allows for the genetic elements and their associated gene products to be isolated from the microcapsules before sorting according to gene product activity takes place. In a preferred embodiment, the complexes are subjected to a further compartmentalisation step prior to isolating the genetic elements encoding a gene product having the desired activity. This further compartmentalisation step, which advantageously takes place in microcapsules, permits the performance of further reactions, under different conditions, in an environment where the genetic elements and their respective gene products are physically linked. Eventual sorting of genetic elements may be performed according to embodiment (I), (II) or (III) above.

The "secondary encapsulation" may also be performed with genetic elements linked to gene products by other means, such as by phage display, polysome display, RNA-peptide fusion or lac repressor peptide fusion.

The selected genetic element(s) may also be subjected to subsequent, possibly more stringent rounds of sorting in iteratively repeated steps, reapplying the method of the invention either in its entirety or in selected steps only. By tailoring the conditions appropriately, genetic elements encoding gene products having a better optimised activity may be isolated after each round of selection.

Additionally, the genetic elements isolated after a first round of sorting may be subjected to mutagenesis before repeating the sorting by iterative repetition of the steps of the method of the invention as set out above. After each round of mutagenesis, some genetic elements will have been modified in such a way that the activity of the gene products is enhanced.

Moreover, the selected genetic elements can be cloned into an expression vector to allow further characterisation of the genetic elements and their products. A multitude of suitable vectors are known to the person skilled in the art. The vectors may be, for example, virus, plasmid or phage vectors provided with an origin of replication, optionally a promoter for the expression of the genetic element and optionally a regulator of the promoter. The vectors may contain a selectable marker gene, for example the neomycin resistance gene for a mammalian vector.

DETAILED DESCRIPTION

Emulsions

Figure 1:
FIG. 1 shows emulsions formed by mixing oil-phase with rabbit reticulocyte lysate (RRL) for 1.5 min and photographed in visual spectrum after 15 min incubation at 30° C. From left to right: 1) CSR mix, 2) CSR mix+DTT, 3) 1.5% Span80 in mineral oil, 4) 1.5% Span80 in mineral oil+DTT, 5) 4% Abil EM90, 6) 4% Abil EM90+DTT

Emulsions are heterogeneous systems of two immiscible liquid phases with one of the phases dispersed in the other as droplets of microscopic or colloidal size (Becher, 1957; Sherman, 1968; Lissant, 1984). Emulsions of the invention must enable the formation of microcapsules.

Emulsions may be produced from any suitable combination of immiscible liquids. The emulsion of the present invention has a hydrophilic phase (containing the biochemical components) as the phase present in the form of finely divided droplets (the disperse, internal or discontinuous phase) and a hydrophobic, immiscible liquid (an 'oil') as the matrix in which these droplets are suspended (the nondisperse, continuous or external phase). Such emulsions are termed 'water-in-oil' (W/O). This has the advantage that the entire aqueous phase containing the biochemical components is compartmentalised in discreet droplets (the internal phase). The external phase, being a hydrophobic oil, generally contains none of the biochemical components and hence is inert.

Creation of an emulsion generally requires the application of mechanical energy to force the phases together. There are a variety of ways of doing this which utilise a variety of mechanical devices, including stirrers (such as magnetic stir-bars, propeller and turbine stirrers, paddle devices and whisks), homogenisers (including rotor-stator homogenisers, high-pressure valve homogenisers and jet homogenisers), colloid mills, ultrasound and 'membrane emulsification' devices (Becher, 1957; Dickinson, 1994).

Desirably, the emulsion is stable during incubation at 30° C. for at least one hour. In some cases it is preferred that it also be stable at higher temperatures, especially if thermal cycling is used during PCR or other amplification procedures.

Surfactants

Emulsions of the invention are stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993).

However, as described in the examples, surfactants conventionally used in emulsions applications such as non-ionic surfactants (Schick, 1966), for example, sorbitan monooleate (Span™80; ICI) and polyoxyethylenesorbitan monooleate (Tween™ 80; ICI) are not suitable for efficient in vitro eukaryotic expression with the rabbit reticulocyte lysate However, as described herein, such expression may be maintained when chemically inert silicone-based surfactants are used.

Preferably, the chemically inert silicone-based surfactant of the emulsion is a silicone copolymer.

More preferably the surfactant comprises a polysiloxane-polycetyl-polyethylene glycol copolymer (Cetyl Dimethicone Copolyol) e.g. Abil.® EM90 (Goldschmidt).

The chemically inert silicone-based surfactant may be provided as the sole surfactant in the emulsion composition or may be provided as one of several surfactants. For example a mixture of different surfactants may be used.

In preferred embodiments, the surfactant is provided at a v/v concentration in the oil phase of the emulsion of 0.5 to 20%, preferably 1 to 10%, more preferably 3-5%.

In a highly preferred embodiment, the surfactant is provided at a v/v concentration in the oil phase of 4%.

In a highly preferred embodiment of the invention the emulsion is made by adding an aqueous phase dropwise to an oil phase in the presence of a surfactant comprising about 3-5% (v/v) polysiloxane-polycetyl-polyethylene glycol copolymer in mineral oil, preferably at a ratio of oil:water phase of 2.5:1.

The surfactant may be present initially with the hydrophobic composition. A composition comprising the surfactant and the hydrophobic composition therefore represents a further aspect of the present invention.

Alternatively, the surfactant may be added at a later stage, e.g. during or following the mixing of the hydrophobic and hydrophilic phases.

In this embodiment the surfactant may be provided in a kit, together with a hydrophobic composition. The kit may optionally also include a eukaryotic expression system such as rabbit reticulocyte lysate and/or a device for mixing the hydrophobic and hydrophilic phases. It may further include instructions for use in providing an emulsion of the present invention Alternatively, the surfactant may be present initially with the hydrophilic composition.

Microcapsules

The term "microcapsule" is synonymous with "compartment" and the terms are used interchangeably. In essence, a microcapsule is an artificial compartment whose delimiting borders restrict the exchange of the components of the molecular mechanisms described herein which allow the sorting of genetic elements according to the function of the gene products which they encode.

The microcapsules formed by the emulsion require appropriate physical properties to allow the working of the invention. In particular, the contents of each microcapsule must be isolated from the contents of surrounding microcapsules.

Preferably, the microcapsules used in the methods of the present invention will be capable of being produced in very large numbers, and thereby to compartmentalise a library of genetic elements which encodes a repertoire of gene products. The function of the microcapsule is to enable co-localisation of the nucleic acid and the corresponding polypeptide encoded by the nucleic acid. This is preferably achieved by the ability of the microcapsule to substantially restrict diffusion of template and product strands to other microcapsules.

Second, the methods of the present invention require that there are only a limited number of genetic elements per microcapsule formed in the emulsion. This ensures that the gene product of an individual genetic element will be isolated from other genetic elements. Thus, coupling between genetic element and gene product will be highly specific. The enrichment factor is greatest with on average one or fewer genetic elements per microcapsule, or two or more copies of a single genetic element per microcapsule, the linkage between nucleic acid and the activity of the encoded gene product being as tight as is possible, since the gene product of an individual genetic element will be isolated from the products of all other genetic elements. However, even if the theoretically optimal situation of, on average, a single genetic element or less per microcapsule is not used, a ratio of 5, 10, 50, 100 or 1000 or more genetic elements per microcapsule may prove beneficial in sorting a large library. Subsequent rounds of sorting, including renewed encapsulation with differing genetic element distribution, will permit more stringent sorting of the genetic elements. Preferably, there is a single genetic element, or fewer, per microcapsule.

Thirdly, the formation and the composition of the microcapsules must not abolish the function of the machinery for the expression of the genetic elements and the activity of the gene products using eukaryotic in vitro expression systems.

Consequently, the microcapsules formed by the emulsion must fulfil these three requirements. The appropriate emulsion may vary depending on the precise nature of the requirements in each application of the invention, as will be apparent to the skilled person.

The preferred microcapsule size will vary depending upon the precise requirements of any individual selection process that is to be performed according to the present invention. In all cases, the principle consideration is the need for required concentration of components in the individual compartments to achieve efficient transcription/translation. This may be balanced with other requirements which may relate to gene library size, enrichment, or sorting procedures.

If small microcapsules are provided, a very large number of discrete microcapsules can be provided within a small volume of emulsion. Furthermore the provision of small microcapsules increases selectivity by increasing the likelihood that only one type of gene product will be produced within a given microcapsule. It is therefore preferred that on average no more than one genetic elements that is to be transcribed and/or translated is present per compartment in order to keep the linkage between nucleic acid and the activity of encoded gene product as tight as is possible. However, even if the theoretically optimal situation of, on average, a single genetic element or less per microcapsule is not used, a ratio of 5, 10, 50, 100 or 1000 or more genetic elements per microcapsule may prove beneficial in sorting a large library. Subsequent rounds of sorting, including renewed encapsulation with differing genetic element distribution, will permit more stringent sorting of the genetic elements. Preferably, there is on average no more than a single genetic element per microcapsule.

Desirably, the mean volume of the microcapsules is less that $5.2 \times 10^{-16}$ m$^3$, (corresponding to a spherical microcapsule of diameter less than 10 µm), more desirably less than $6.5 \times 10^{-17}$ m$^3$ (corresponding to a spherical microcapsule of diameter less than 5 µm), still more desirably about $4.2 \times 10^{-18}$ m$^3$ (corresponding to a spherical microcapsule of diameter of approximately 2 µm).

The effective DNA or RNA concentration in microcapsules may be artificially increased by various methods that will be well-known to those versed in the art. These include, for example, the addition of volume excluding chemicals such as polyethylene glycols (PEG) and a variety of gene amplification techniques, including transcription using RNA polymerases including those from bacteria such as E. coli (Roberts, 1969; Blattner and Dahlberg, 1972; Roberts et al., 1975; Rosenberg et al., 1975, eukaryotes e.g. (Weil et al., 1979; Manley et al., 1983) and bacteriophage such as T7, T3 and SP6 (Melton et al., 1984); the polymerase chain reaction (PCR) (Saiki et al., 1988); Qβ replicase amplification (Miele et al., 1983; Cahill et al., 1991; Chetverin and Spirin, 1995; Katanaev et al., 1995); the ligase chain reaction (LCR) (Landegren et al., 1988; Barany, 1991); and self-sustained sequence replication system (Fahy et al., 1991) and strand displacement amplification (Walker et al., 1992). Gene amplification techniques advantageously using thermal cycling (such as PCR and LCR) may be used if the emulsions and the in vitro transcription or coupled transcription-translation systems are thermostable.

Increasing the effective local nucleic acid concentration enables microcapsules to be used more effectively. Thus microcapsules having volumes of up to only about $5.2 \times 10^{-16}$ m$^3$ (corresponding to a sphere of diameter 10 µl) can be used for many purposes, although of course microcapsules with larger volumes can be used, if desired.

The microcapsule size must be sufficiently large to accommodate all of the required components of the biochemical reactions that are needed to occur within the microcapsule. For example, in vitro, both transcription reactions and coupled transcription-translation reactions often require a total nucleoside triphosphate concentration of about 2 mM.

It can also be noted that, in order to transcribe a gene to a single short RNA molecule of 500 bases in length, this would require a minimum of 500 molecules of nucleoside triphosphate per microcapsule ($8.33 \times 10^{-22}$ moles). In order to constitute a 2 mM solution, this number of molecules must be contained within a microcapsule of volume $4.17 \times 10^{-19}$ litres ($4.17 \times 10^{-22}$ m$^3$), which, if spherical, would have a diameter of 93 nm.

Furthermore, particularly in the case of reactions involving translation, it is to be noted that the eukaryotic ribosomes necessary for the translation to occur are themselves approximately 30 nm in diameter. Hence, the preferred lower limit for microcapsules is a diameter of approximately 0.1 µm (100 nm).

Therefore, the microcapsule volume is preferably of the order of between $5.2 \times 10^{-22}$ m$^3$ and $5.2 \times 10^{-16}$ m$^3$ corresponding to a sphere of diameter between 0.1 µm and 10 µm, more preferably of between about $5.2 \times 10^{-19}$ m$^3$ and $6.5 \times 10^{-17}$ m$^3$ (1 µm and 5 µm).

Although small microcapsules are preferred for certain applications, such as the methods disclosed in WO99/02671, it is important to note that the present invention is in no way limited to the provision of small microcapsules and that transcription and translation systems also function in large microcapsules.

The size of emulsion microcapsules may be varied simply by tailoring the emulsification conditions used to form the emulsion according to requirements of the selection system.

Compartment size may be varied (within limits of emulsion stability and inactivation of RRL) by 1) increased mixing time, 2) different W/O ratios, 3) different concentrations of surfactant.

The size distribution of microcapsules in emulsions can be determined by any method known to skilled person. For example, the size distribution may be assessed using laser diffraction (e.g. using a Coulter LS230 Particle Size Analyser) or by microscopic examination.

Expression

"Expression", as used herein, is used in its broadest meaning, to signify that a nucleic acid contained in the genetic element is converted into its gene product. Thus, where the nucleic acid is DNA, expression refers to the transcription of the DNA into RNA; where this RNA codes for protein, "expression" may also refer to the translation of the RNA into protein. Where the nucleic acid is RNA, "expression" may refer to the replication of this RNA into further RNA copies, the reverse transcription of the RNA into DNA and optionally the transcription of this DNA into further RNA molecule(s), as well as optionally the translation of any of the RNA species produced into protein. Preferably, therefore, "expression" is performed by one or more processes selected from the group consisting of transcription, reverse transcription, replication and translation.

"Expression" of the genetic element may thus be directed into either DNA, RNA or protein, or a nucleic acid or protein containing unnatural bases or amino acids (the gene product) within the microcapsule of the invention, so that the gene product is confined within the same microcapsule as the genetic element.

Expression Systems

Any appropriate in vitro eukaryotic expression system can be used in the emulsion of the invention provided that it includes components needed for transcription and/or translation. If glycosylation is desired then one or more glycosylases can also be present, as appropriate, in order to achieve a desired glycosylation pattern.

The expression system may, for example, comprise all or part of a cell lysate or extract.[For example wheat germ extract may be used (Anderson et al., 1983) and is available commercially from Promega. Desirably, however, the cell lysate is a mammalian cell lysate. It may be a reticulocyte lysate. A preferred reticulocyte lysate is a rabbit reticulocyte lysate (an "RRL"). The RRL system is well characterised (see e.g. Pelham and Jackson, 1976) and is available commercially from Promega.

However, any convenient eukaryotic expression system prepared from other cell extracts may be used. The extracts should contain all the components required for translation of RNA (e.g. ribosomes, tRNAs, aminoacyl-tRNA synthetases, initiation, elongation and termination factors etc with the extracts preferably supplemented with amino acids, ATP, GTP, creatine phosphate and creatine phosphokinase, other co-factors such as $Mg^{2+}$.

By using emulsions of the present invention it is possible to obtain appreciable expression of a genetic element and/or activity of a gene product using an in vitro eukaryotic expression system present within an emulsion. Expression and/or activity is desirably at a level of at least 1% of that of the gene product achievable with the expression system prior to formation of the emulsion. More preferably it is at least 10%, 20% or 30% of said level and/or activity.

Genetic Elements

A "genetic element" is a molecule or molecular construct comprising a nucleic acid. The genetic elements of the present invention may comprise any nucleic acid (for example, DNA, RNA or any analogue, natural or artificial, thereof).

Nucleic acids encoding any appropriate gene product can be used in the in vitro transcription and/or translation systems. In addition to coding sequences, the nucleic acids may, for example, comprise promoters, operators, enhancers, translational and transcriptional initiation and termination sequences, polyadenylation sequences, splice sites, upstream and downstream regulatory regions, etc., as required for transcription and/or translation. In some cases it may be preferred to use inducible and/or temperature sensitive promoters in order to ensure expression occurs only at a particular stage.

The nucleic acid component of the genetic element may moreover be linked, covalently or non-covalently, to one or more molecules or structures, including polypeptides, peptides, chemical entities and groups, solid-phase supports such as magnetic beads, and the like. In the methods of the invention, these structures or molecules can be designed to assist in the sorting and/or isolation of the genetic element encoding a gene product with the desired activity.

As will be apparent from the following, in many cases the polypeptide or other molecular group or construct is a ligand or a substrate which directly or indirectly binds to or reacts with the gene product in order to tag the genetic element. This allows the sorting of the genetic element on the basis of the activity of the gene product.

The ligand or substrate can be connected to the nucleic acid by a variety of means that will be apparent to those skilled in the art (see, for example, Hermanson, 1996). Any tag will suffice that allows for the subsequent selection of the genetic element. Sorting can be by any method which allows the preferential separation, amplification or survival of the tagged genetic element. Examples include selection by binding (including techniques based on magnetic separation, for example using Dynabeads™), and by resistance to degradation (for example by nucleases, including restriction endonucleases).

One way in which the nucleic acid molecule may be linked to a ligand or substrate is through biotinylation. This can be done by PCR amplification with a 5'-biotinylation primer such that the biotin and nucleic acid are covalently linked. A biotinylated nucleic acid may be coupled to a polystyrene microbead (0.035 to 0.2 μm in diameter) that is coated with avidin or streptavidin, that will therefore bind the nucleic acid with very high affinity. This bead can be derivatised with substrate or ligand by any suitable method such as by adding biotinylated substrate or by covalent coupling.

Alternatively, a biotinylated nucleic acid may be coupled to avidin or streptavidin complexed to a large protein molecule such as thyroglobulin (669 Kd) or ferritin (440 Kd). This complex can be derivatised with substrate or ligand, for example by covalent coupling to the-amino group of lysines or through a non-covalent interaction such as biotin-avidin. The substrate may be present in a form unlinked to the genetic element but containing an inactive "tag" that requires a further step to activate it such as photoactivation (e.g. of a "caged" biotin analogue, (Sundberg et al., 1995; Pirrung and Huang, 1996)). The catalyst to be selected then converts the substrate to product. The "tag" could then be activated and the "tagged" substrate and/or product bound by a tag-binding molecule (e.g. avidin or streptavidin) complexed with the nucleic acid. The ratio of substrate to product attached to the nucleic acid via the "tag" will therefore reflect the ratio of the substrate and product in solution.

An alternative is to couple the nucleic acid to a product-specific antibody (or other product-specific molecule). In this scenario, the substrate (or one of the substrates) is present in each microcapsule unlinked to the genetic element, but has a molecular "tag" (for example biotin, DIG or DNP). When a catalyst to be selected converts the substrate to product, the product retains the "tag" and is then captured in the microcapsule by the product-specific antibody. In this way the genetic element only becomes associated with the "tag" when it encodes or produces an enzyme capable of converting substrate to product.

When all reactions are stopped and the microcapsules are combined, the genetic elements encoding active enzymes can be enriched using an antibody or other molecule which binds, or reacts specifically with the "tag". Although both substrates and product have the molecular tag, only the genetic elements encoding active gene product will co-purify.

In a highly preferred application, the methods of the present invention are useful for sorting libraries of genetic elements. The invention accordingly provides a method according to preceding aspects of the invention, wherein the genetic elements are isolated from a library of genetic elements encoding a repertoire of gene products. Herein, the terms "library", "repertoire" and "pool" are used according to their ordinary signification in the art, such that a library of genetic elements encodes a repertoire of gene products. In general, libraries are constructed from pools of genetic elements and have properties which facilitate sorting.

Initial selection of a genetic element from a genetic element library using the present invention will in most cases require the screening of a large number of variant genetic elements. Libraries of genetic elements can be created in a variety of different ways, including the following.

Pools of naturally occurring genetic elements can be cloned from genomic DNA or cDNA (Sambrook et al., 1989); for example, phage antibody libraries, made by PCR amplification repertoires of antibody genes from immunised or unimmunised donors have proved very effective sources of functional antibody fragments (Winter et al., 1994; Hoogenboom, 1997). Libraries of genes can also be made by encoding all (see for example Smith, 1985; Parmley and Smith, 1988) or part of genes (see for example Lowman et al., 1991) or pools of genes (see for example Nissim et al., 1994) by a randomised or doped synthetic oligonucleotide. Libraries can also be made by introducing mutations into a genetic element or pool of genetic elements 'randomly' by a variety of techniques in vivo, including; using 'mutator strains', of bacteria such as *E. coli* mutD5 (Liao et al., 1986; Yamagishi et al., 1990; Low et al., 1996); using the antibody hypermutation system of B-lymphocytes (Yelamos et al., 1995). Random mutations can also be introduced both in vivo and in vitro by chemical mutagens, and ionising or UV irradiation (see Friedberg et al., 1995), or incorporation of mutagenic base analogues (Freese, 1959; Zaccolo et al., 1996). 'Random' mutations can also be introduced into genes in vitro during polymerisation for example by using error-prone polymerases (Leung et al., 1989).

Further diversification can be introduced by using homologous recombination either in vivo (see Kowalczykowski et al., 1994) or in vitro (Stemmer, 1994a; Stemmer, 1994b).

Gene Product

The present invention can thus be used to produce specific, desired gene products or to produce a range of diverse gene products (which may be partially or wholly unknown) for screening purposes.

The term "gene product" is used herein in its broadest sense to include not only polypeptides but also RNA gene products. Thus it includes the products of transcription alone, as well as the products of both transcription and translation.

Preferred gene products are polypeptides that occur naturally in eukaryotic cells (especially mammalian or human cells) but not in prokaryotic cells, or mutant forms of such polypeptides having one or more amino acid changes relative to the wild type eukaryotic polypeptide. Mutant forms are useful in generating diversity, e.g. for screening purposes. However, if amino acid changes are made it is preferred that there is a limited number of such changes, e.g. that less than 50, less than 25, less than 10 or less than 5 amino acids are changed relative to a wild type polypeptide. Mutant forms may, for example, act as antagonists or agonists of one or more of the biological activities of a wild-type polypeptide. They may therefore be useful in studying structure-function relationships, in screening, in drug development programs, etc. Mutations can be introduced into nucleic acids by any appropriate method. For example, a nucleic acid sequence incorporating a desired sequence change can be provided by site-directed mutagenesis. This can then be used to allow the expression of an RNA or a polypeptide having a corresponding change in its sequence. Alternatively, a nucleic acid may be synthesised to include a given mutation. Mutations can also be provided by using mutagenic agents and/or irradiation.

For certain applications the expression system may be used to express a gene product useful in the replication, repair, maintenance or replication of a nucleic acid of a eukaryotic cell, preferably of a mammalian or human cell. The gene product may therefore have activity as a polymerase, a reverse transcriptase, a ligase, or a telomerase, for example. It may have more than one such activity. If it is involved in nucleic acid repair, it may have proofreading activity.

Gene products can be produced in the compartments formed by the hydrophilic phase of the emulsion and containing the expression system.

Selection Procedures

The methods can be configured to select for RNA, DNA or protein gene product molecules with catalytic, regulatory or binding activity.

(i) Affinity Selection

In the case of selection for a gene product with affinity for a specific ligand the genetic element may be linked to the gene product in the microcapsule via the ligand. Only gene products with affinity for the ligand will therefore bind to the genetic element itself and therefore only genetic elements that produce active product will be retained in the selection step. In this embodiment, the genetic element will thus comprise a nucleic acid encoding the gene product linked to a ligand for the gene product.

In this embodiment, all the gene products to be selected contain a putative binding domain, which is to be selected for, and a common feature—a tag. The genetic element in each microcapsule is physically linked to the ligand. If the gene product produced from the genetic element has affinity for the ligand, it will bind to it and become physically linked to the same genetic element that encoded it, resulting in the genetic element being 'tagged'. At the end of the reaction, all of the microcapsules are combined, and all genetic elements and gene products pooled together in one environment. Genetic elements encoding gene products exhibiting the desired binding can be selected by affinity purification using a molecule that specifically binds to, or reacts specifically with, the "tag".

In an alternative embodiment, genetic elements may be sorted on the basis that the gene product, which binds to the ligand, merely hides the ligand from, for example, further binding partners. In this eventuality, the genetic element, rather than being retained during an affinity purification step, may be selectively eluted whilst other genetic elements are bound.

In an alternative embodiment, the invention provides a method according to the second aspect of the invention, wherein in step (b) the gene products bind to genetic elements encoding them. The gene products together with the attached genetic elements are then sorted as a result of binding of a ligand to gene products having the desired activity. For example, all gene products can contain an invariant region which binds covalently or non-covalently to the genetic element, and a second region which is diversified so as to generate the desired binding activity.

Sorting by affinity is dependent on the presence of two members of a binding pair in such conditions that binding may occur. Any binding pair may be used for this purpose. As used herein, the term binding pair refers to any pair of molecules capable of binding to one another. Examples of binding pairs that may be used in the present invention include an antigen and an antibody or fragment thereof capable of binding the antigen, the biotin-avidin/streptavidin pair (Savage et al., 1994), a calcium-dependent binding polypeptide and ligand thereof (e.g. calmodulin and a calmodulin-binding peptide (Stofko et al., 1992; Montigiani et al., 1996)), pairs of polypeptides which assemble to form a leucine zipper (Tripet et al., 1996), histidines (typically hexahistidine peptides) and chelated $Cu^{2+}$, $Zn^{2+}$ and $Ni^{2+}$, (e.g. Ni-NTA; Hochuli et al., 1987), RNA-binding and DNA-binding proteins (Klug, 1995) including those containing zinc-finger motifs (Klug and Schwabe, 1995) and DNA methyltransferases (Anderson, 1993), and their nucleic acid binding sites.

However, the usefulness of certain affinity based selection methods may be limited. Especially with low to medium affinity interactions, the half-life of the interactions may often be too short compared with the time required to detect the interactions.

Thus in one embodiment of the present invention, selection methods are based on increasing the affinity of intermolecular interactions by allowing multivalent interactions to occur. The resulting apparent increase in affinity gained by multivalent interaction, also termed avidity, is due to the fact that when two or more binding interactions take place within the same molecular complex, there is only a very small additional entropic price to be paid for the second or further interactions. This is because most degrees of freedom have already been lost when binding through one binding site immobilised the multivalent ligand. However, avidity can have particularly drastic effects on the dissociation kinetics ($k_{off}$), as all interactions must be broken before dissociation can take place.

Thus, in this embodiment, molecules that interact may be selected by allowing multivalent interactions to occur between the molecules, thus increasing the stability of any complex formed as compared with a corresponding monovalent interaction.

Preferably, the first and/or second interacting molecules, e.g. the gene product and the ligand molecule to which it binds, have been modified to increase their valency. Preferably, one or more reactive groups is present on the gene product or ligand molecules, or both, such that the gene product (and/or ligand) molecules associate with each other to form multivalent gene product complexes and/or multivalent ligand molecule complexes. The multivalent complexes may then be selected for binding according to the invention. Preferably, the reactive groups form a covalent bond on interaction.

The term "multivalent complex" as used herein means a molecular complex comprising (i) at least two molecules of the gene product or at least one molecule of a multivalent gene product and (ii) a multivalent ligand molecule, wherein the at least two molecules of the gen product are interacting with the ligand molecule or the at least one molecule of a multivalent gen product is interacting with the ligand molecule via at least two valencies.

In such avidity selection procedures, the ligand molecule is preferably multivalent. For example, where the ligand molecule is a polypeptide, the ligand molecule may be multivalent by virtue of being expressed as a fusion protein to a third polypeptide which multimerises.

The gene product and/or ligand molecules may comprise a tag, for example a biotin or a myc epitope tag or moiety, to assist in purifying complexes formed between them, and/or to assist in recovering gene product and/or ligand molecules for analysis and identification.

The ligand molecule is typically a multimer, such as a dimer, or capable of forming a homomultimer under the reaction conditions used in the methods of the invention. Alternatively, the ligand molecule may be a heteromultimer. It is preferred to use ligand molecules which are polypeptides that have been engineered to be multimeric but whose constituent subunits do not normally form multimers. This may be achieved by chemical linkage of two or more molecules to form a covalently linked multimer. Alternatively, in the case of ligand moleculoes which are polypeptides and which bind to gene products which are polypeptides, the molecules may be expressed as a fusion to a third polypeptide, the third polypeptide forming homomultimers which effectively results in multimerisation of the fused ligand polypeptide sequence. An example of a suitable third polypeptide (referred to herein as a "hook" polypeptide) is glutathione-S-transferase (GST), which forms dimers. Preferred hook polypeptides provide for good levels of expression of soluble products. In one embodiment, hook polypeptides that are suitable for secretion into the bacterial periplasm (e.g. GST after the removal of 3 surface Cys residues (Tudyka and Skerra, 1997) are preferred. The ligand molecule may be provided as a plurality of ligand molecules.

In a particularly preferred embodiments of the invention, the gene products are polypeptides encoded by first polynucleotides and the polynucleotides are associated with the corresponding polypeptides such that when a first polypeptide is selected during the screening methods of the present invention, the polynucleotide sequence that encodes the selected polypeptide is physically linked, or in close proximity, and can easily be recovered and, for example, sequenced to determine the identity of the selected polypeptide. In order to achieve this, the plurality of first polynucleotides in a compartment may be such that there is on average only one polynucleotide per using the emulsion of the present invention.

Further details of avidity based selection methods, which may be used in methods of the present invention, are described in co-pending GB patent application 0114856.8, the contents of which are herein incorporated by reference.

(ii) Catalysis

When selection is for catalysis, the genetic element in each microcapsule may comprise the substrate of the reaction. If the genetic element encodes a gene product capable of acting as a catalyst, the gene product will catalyse the conversion of the substrate into the product. Therefore, at the end of the reaction the genetic element is physically linked to the product of the catalysed reaction. When the microcapsules are combined and the reactants pooled, genetic elements encoding catalytic molecules can be enriched by selecting for any property specific to the product.

For example, enrichment can be by affinity purification using a molecule (e.g. an antibody) that binds specifically to the product. Equally, the gene product may have the effect of modifying a nucleic acid component of the genetic element, for example by methylation (or demethylation) or mutation of the nucleic acid, rendering it resistant to or susceptible to attack by nucleases, such as restriction endonucleases.

Alternatively, selection may be performed indirectly by coupling a first reaction to subsequent reactions that takes place in the same microcapsule. There are two general ways in which this may be performed. First, the product of the first reaction could be reacted with, or bound by, a molecule which does not react with the substrate of the first reaction. A second, coupled reaction will only proceed in the presence of the product of the first reaction. An active genetic element can then be purified by selection for the properties of the product of the second reaction.

Alternatively, the product of the reaction being selected may be the substrate or cofactor for a second enzyme-catalysed reaction. The enzyme to catalyse the second reaction can either be translated in situ in the microcapsules or incorporated in the reaction mixture prior to microencapsulation. Only when the first reaction proceeds will the coupled enzyme generate a selectable product.

This concept of coupling can be elaborated to incorporate multiple enzymes, each using as a substrate the product of the previous reaction. This allows for selection of enzymes that will not react with an immobilised substrate. It can also be designed to give increased sensitivity by signal amplification if a product of one reaction is a catalyst or a cofactor for a second reaction or series of reactions leading to a selectable product (for example, see Johannsson and Bates, 1988; Johannsson, 1991). Furthermore an enzyme cascade system can be based on the production of an activator for an enzyme or the destruction of an enzyme inhibitor (see Mize et al., 1989). Coupling also has the advantage that a common selection system can be used for a whole group of enzymes which generate the same product and allows for the selection of complicated chemical transformations that cannot be performed in a single step.

Such a method of coupling thus enables the evolution of novel "metabolic pathways" in vitro in a stepwise fashion, selecting and improving first one step and then the next. The selection strategy is based on the final product of the pathway, so that all earlier steps can be evolved independently or sequentially without setting up a new selection system for each step of the reaction.

Expressed in an alternative manner, there is provided a method of isolating one or more genetic elements encoding a gene product having a desired catalytic activity, comprising the steps of:

(1) expressing genetic elements to give their respective gene products;
(2) allowing the gene products to catalyse conversion of a substrate to a product, which may or may not be directly selectable, in accordance with the desired activity;
(3) optionally coupling the first reaction to one or more subsequent reactions, each reaction being modulated by the product of the previous reactions, and leading to the creation of a final, selectable product;
(4) linking the selectable product of catalysis to the genetic elements by either:
   a) coupling a substrate to the genetic elements in such a way that the product remains associated with the genetic elements, or
   b) reacting or binding the selectable product to the genetic elements by way of a suitable molecular "tag" attached to the substrate which remains on the product, or
   c) coupling the selectable product (but not the substrate) to the genetic elements by means of a product-specific reaction or interaction with the product; and
(5) selecting the product of catalysis, together with the genetic element to which it is bound, either by means of a specific reaction or interaction with the product, or by affinity purification using a suitable molecular "tag" attached to the product of catalysis, wherein steps (1) to (4) each genetic element and respective gene product is contained within a microcapsule formed from an emulsion of the invention.

(iii) Regulation

A similar system can be used to select for regulatory properties of enzymes.

In the case of selection for a regulator molecule which acts as an activator or inhibitor of a biochemical process, the components of the biochemical process can either be translated in situ in each microcapsule or can be incorporated in the reaction mixture prior to microencapsulation. If the genetic element being selected is to encode an activator, selection can be performed for the product of the regulated reaction, as described above in connection with catalysis. If an inhibitor is desired, selection can be for a chemical property specific to the substrate of the regulated reaction.

There is therefore provided a method of sorting one or more genetic elements coding for a gene product exhibiting a desired regulatory activity, comprising the steps of:

(1) expressing genetic elements to give their respective gene products;
(2) allowing the gene products to activate or inhibit a biochemical reaction, or sequence of coupled reactions, in accordance with the desired activity, in such a way as to allow the generation or survival of a selectable molecule;
(3) linking the selectable molecule to the genetic elements either by
   a) having the selectable molecule, or the substrate from which it derives, attached to the genetic elements, or
   b) reacting or binding the selectable product to the genetic elements, by way of a suitable molecular "tag" attached to the substrate which remains on the product, or
   c) coupling the product of catalysis (but not the substrate) to the genetic elements, by means of a product-specific reaction or interaction with the product;
(4) selecting the selectable product, together with the genetic element to which it is bound, either by means of a specific reaction or interaction with the selectable product, or by affinity purification using a suitable molecular "tag" attached to the product of catalysis.

wherein steps (1) to (4) each genetic element and respective gene product is contained within a microcapsule formed by an emulsion of the invention.

(iv) Microcapsule Sorting

The invention provides for the sorting of intact microcapsules where this is enabled by the sorting techniques being employed. Microcapsules may be sorted as such when the change induced by the desired gene product either occurs or manifests itself at the surface of the microcapsule or is detectable from outside the microcapsule. The change may be caused by the direct action of the gene product, or indirect, in which a series of reactions, one or more of which involve the gene product having the desired activity leads to the change. For example, the microcapsule may be so configured that the gene product is displayed at its surface and thus accessible to reagents. Where the microcapsule is a membranous microcapsule, the gene product may be targeted or may cause the targeting of a molecule to the membrane of the microcapsule. This can be achieved, for example, by employing a membrane localisation sequence, such as those derived from membrane proteins, which will favour the incorporation of a fused or linked molecule into the microcapsule membrane. Alternatively, where the microcapsule is formed by phase partitioning such as with water-in-oil emulsions, a molecule having parts which are more soluble in the extra-capsular phase will arrange themselves such that they are present at the boundary of the microcapsule.

In a preferred aspect of the invention, however, microcapsule sorting is applied to sorting systems which rely on a change in the optical properties of the microcapsule, for example absorption or emission characteristics thereof, for example alteration in the optical properties of the microcapsule resulting from a reaction leading to changes in absorbance, luminescence, phosphorescence or fluorescence associated with the microcapsule. All such properties are included in the term "optical". In such a case, microcapsules can be sorted by luminescence, fluorescence or phosphorescence activated sorting. In a highly preferred embodiment, fluorescence activated sorting is employed to sort microcapsules in which the production of a gene product having a desired activity is accompanied by the production of a fluorescent molecule in the capsule. For example, the gene product itself may be fluorescent, for example a fluorescent protein such as GFP. Alternatively, the gene product may induce or modify the fluorescence of another molecule, such as by binding to it or reacting with it.

(v) Microcapsule Identification

Microcapsules may be identified by virtue of a change induced by the desired gene product which either occurs or manifests itself at the surface of the microcapsule or is detectable from the outside as described in section (iv) (Microcapsule Sorting). This change, when identified, is used to trigger the modification of the gene within the compartment. In a preferred aspect of the invention, microcapsule identification relies on a change in the optical properties of the microcapsule resulting from a reaction leading to luminescence, phosphorescence or fluorescence within the microcapsule. Modification of the gene within the microcapsules would be triggered by identification of luminescence, phosphorescence or fluorescence. For example, identification of luminescence, phosphorescence or fluorescence can trigger bombardment of the compartment with photons (or other particles or waves) which leads to modification of the genetic element. A similar procedure has been described previously for the rapid sorting of cells (Keij et al., 1994). Modification of the genetic element may result, for example, from coupling a molecular "tag", caged by a photolabile protecting group to the genetic elements: bombardment with photons of an appropriate wavelength leads to the removal of the cage. Afterwards, all microcapsules are combined and the genetic elements pooled together in one environment. Genetic elements encoding gene products exhibiting the desired activity can be selected by affinity purification using a molecule that specifically binds to, or reacts specifically with, the "tag".

(vi) Multi-Step Procedure

It will be also be appreciated that according to the present invention, it is not necessary for all the processes of transcription/replication and/or translation, and selection to proceed in one single step, with all reactions taking place in one microcapsule. The selection procedure may comprise two or more steps. First, transcription/replication and/or translation of each genetic element of a genetic element library may take place in a first microcapsule. Each gene product is then linked to the genetic element which encoded it (which resides in the same microcapsule). The microcapsules are then broken, and the genetic elements attached to their respective gene products optionally purified. Alternatively, genetic elements can be attached to their respective gene products using methods which do not rely on encapsulation. For example phage display (Smith, G. P., 1985), polysome display (Mattheakkis et al., 1994), RNA-peptide fusion (Roberts and Szostak, 1997) or lac repressor peptide fusion (Cull, et al., 1992).

In the second step of the procedure, each purified genetic element attached to its gene product is put into a second microcapsule containing components of the reaction to be selected. This reaction is then initiated. After completion of the reactions, the microcapsules are again broken and the modified genetic elements are selected. In the case of complicated multistep reactions in which many individual components and reaction steps are involved, one or more intervening steps may be performed between the initial step of creation and linking of gene product to genetic element, and the final step of generating the selectable change in the genetic element.

(vii) Selection by Activation of Reporter Gene Expression In Situ

The system can be configured such that the desired binding, catalytic or regulatory activity encoded by a genetic element leads, directly or indirectly to the activation of expression of a "reporter gene" that is present in all microcapsules. Only gene products with the desired activity activate expression of the reporter gene. The activity resulting from reporter gene expression allows the selection of the genetic element (or of the compartment containing it) by any of the methods described herein.

For example, activation of the reporter gene may be the result of a binding activity of the gene product in a manner analogous to the "two hybrid system" (Fields and Song, 1989). Activation might also result from the product of a reaction catalysed by a desirable gene product For example, the reaction product could be a transcriptional inducer of the reporter gene. For example arabinose could be used to induce transcription from the araBAD promoter. The activity of the desirable gene product could also result in the modification of a transcription factor, resulting in expression of the reporter gene. For example, if the desired gene product is a kinase or phosphatase the phosphorylation or dephosphorylation of a transcription factor may lead to activation of reporter gene expression.

(viii) Amplification

According to further aspects of methods of the present invention the methods may comprise the further step of amplifying the genetic elements. Selective amplification may be used as a means to enrich for genetic elements encoding the desired gene product.

19

In all the above configurations, genetic material comprised in the genetic elements may be amplified and the process repeated in iterative steps. Amplification may be by the polymerase chain reaction (Saiki et al., 1988) or by using one of a variety of other gene amplification techniques including; Qβ replicase amplification (Cahill, Foster and Mahan, 1991; Chetverin and Spirin, 1995; Katanaev, Kumasov and Spirin, 1995); the ligase chain reaction (LCR) (Landegren et al., 1988; Barany, 1991); the self-sustained sequence replication system (Fahy, Kwoh and Gingeras, 1991) and strand displacement amplification (Walker et al., 1992).

EXAMPLES

Example 1

Conventional Emulsions do not Support Efficient Eukaryotic In Vitro Translation

An oil phase formulation comprising 4.5% v/v sorbitan monooleate (Span 80, Fluka; 85548) and 0.4% v/v polyoxyethylenesorbitan monooleate (Tween 80, Sigma Ultra; P-8074, and 0.05% v/v t-octylphenoxypolyethoxyethanol (Triton-X 100, Sigma), in mineral oil (Sigma; M-3516) ("original CSR mix") was used to emulsify a RRL expression reaction. All RRL reactions were performed using the TNT T7 quick coupled transcription/translation system (Promega)) expressing firefly luciferase from a plasmid template. A 50 µl expression reaction was set up on ice comprising 80% RRL (v/v), methionine 0.02 mM, and luciferase plasmid template (1 ug). A 40 µl aliquot of this was emulsified by dropwise addition (1 drop per 5 secs) to 100 µl of ice-chilled oil phase under constant stirring (1000 rpm). After addition of the last drop (approximately 20 secs) stirring was continued for an additional 3-4 minutes.

Emulsified reactions were incubated at 30° C. for 1 hour and extracted using ether as described above. Luciferase activity was measured in a 96-well plate reader using luciferase assay reagent (Promega). The non-emulsified reaction was also extracted with ether to enable just comparison of activities. This showed expression levels within emulsion to be typically a very low 0.1% that of the non-emulsified reaction.

Using a "reduced" oil phase formulation, comprising 1.5% (v/v) Span 80 (SIGMA) in mineral oil (SIGMA), slightly improved yields of up to 0.7% were noted, especially with addition of DTT to 20 µM. Inclusion of DTT using the original CSR oil mix was extremely detrimental to emulsion formation. Several ratios of aqueous phase to oil phase were tested, and mixing times varied. The conditions described above gave highest activity with retention of emulsion integrity over the incubation period.

Thus emulsification of a RRL reaction using the "classic" emulsion formulations based on Span80 either alone or in combination with Tween80 and TritonX-100 resulted in a complete loss of in vitro translation activity (<1% as expression outside emulsion (Table 2)) as judged by expression of the enzyme firefly luciferase.

Furthermore, we noted a colour change of the hemin component of the RRL from a dark pink to a rusty brown colour within a matter of minutes after emulsification (see FIG. 1), indicating oxidation of the hemin, presumably attributable to a component of the oil phase.

20

Example 2

Anti-Oxidants do not Restore Efficient Eukaryotic In Vitro Translation

Mammalian translation is regulated, inter alia, by the family of eIF-2a kinases in response to cellular stress (reviewed by Dever (1999), TIBS, 24, 398-403). eIF-2α kinases contain a sensor domain and a conserved eIF2 kinase domain. Their function is to phosphorylate eIF-2α (which shuts down translation) in response to stimuli received through the sensor domain. This serves to protect the cell in circumstances of cellular stress from wasting resources (protein translation consumes large amounts of cellular energy) or as an anti-viral defence by preventing expression of the viral genome. Four different kinases are known to respond to different types of stress signals (Table 1).

TABLE 1

| Stress-responsive eIF2 kinases | |
|---|---|
| Name | Activating signal |
| HRI | oxidative stress (low heme) |
| PKR | viral infection (dsRNA) |
| GCN2 | starvation (low amino acids, uncharged tRNA) |
| PERK | heat stress, viral infection (unfolded protein) |

We reasoned that one of the reasons for the complete shut down in translation (given the discoloring of the hemin in the RRL) was oxidative stress caused by the diffusion of oxidative species from the oil into the water-phase.

The component responsible for discoloration and the inhibition of translation was identified to be contained in both the Span80 and Tween80 surfactant but not in the mineral oil.

We tried to buffer the redox change by providing anti-oxidant or reducing compounds within the oil-phase (BDH, BDA) and/or the water-phase (DTT, ascorbic acid). Furthermore, we tried to remove oxidative species from the oil-phase by reaction of the oil-phase (the mineral oil surfactant mixture) or Span80 alone with (Polystyrylmethyl)trimethylammonium borohydride-beads (Novabiochem) or DTT prior to emulsification. Although slowing discoloration (FIG. 1), this yielded only slight improvements in translation efficiencies (Table 2). Furthermore, treatment of the oil-phase with borohydride-beads appeared to reduce the emulsion-forming properties of the surfactant/oil-phase leading to much destabilized emulsions.

Only DTT (at 20 µM final conc.) produced a slight but consistent improvement in expression levels within emulsion compared to that of non-emulsified reaction (Table 2)). Higher levels of DTT proved detrimental to the RRL expression system (not shown). In general DTT also proved destabilizing to the emulsions.

Example 3

Neither cAMP Nor 2-AP Enable Efficient Eukaryotic In Vitro Translation

We also attempted a direct inhibition of the eIF2 kinase pathway using cAMP or 2-aminopurine (2-AP). Although cAMP produced a small improvement when used on its own, it proved not-additive with the beneficial effects of DTT (not shown). Both cAMP and 2-AP are rather unspecific inhibitors of eIF2 kinases (there are at present no available specific inhibitors) and presumably interfere with other processes within the RRL translation system.

Example 4

Neither HSP70 Nor HSP90 Enable Efficient Eukaryotic In Vitro Translation

The fact that even high concentrations of DTT did not rescue more than residual translation activity suggested to us that other factors than oxidation must be contributing to translation inhibition. One suspect was protein denaturation as affected by the emulsification process, i.e. the vigorous mixing of a hydrophilic water phase and hydrophobic oil-phase. Indeed, it has been known for some time that addition of BSA (presumably containing some denatured protein produced by freeze-thawing) produces a translation shutdown (Matts et al (1993), Biochemistry, 32, 7323-7328), even without emulsification. We confirmed the results of Matts 93 with and without emulsification. We also tried to buffer the effect by supplementing the RRL lysates with chaperones, in particular HSP70 and HSP90 (SIGMA). Once again this produced only small (non additive) improvements (not shown), which could be equalled or surpassed by the addition of small amounts (5%) of glycerol (not shown), which is known to protect proteins from denaturation.

Example 5

Development of a Novel Oil-Phase and Water-In-Oil Emulsion

Given this low level of activity, efforts were made to identify a novel oil phase formulation with diminished potential to cause oxidative stress or protein denaturation during the emulsification process.

After attempts to improve activity with Span80 based emulsions had failed we tested novel surfactants.

Emulsification reactions were performed as described in Example 1, but substituting the surfactants used in that reaction (Span 80, Tween 80, and Triton) with silicone-based surfactants. Of these, chemically inert silicone-based surfactants were found to be successful.

Figure 2:
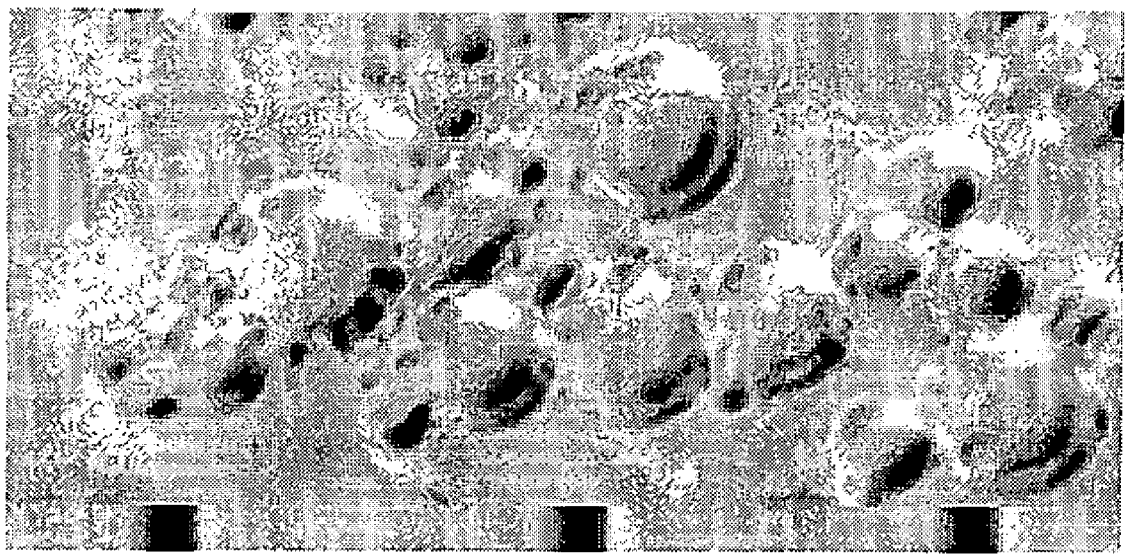
FIG. 2 shows a 4% Abil EM90 in mineral oil emulsion imaged in phase-contrast mode. The distance between the bars is 10 µM

Polysiloxane-polycetyl-polyethylene glycol copolymer (ABIL EM90) (Goldschmidt) used at 4% (v/v) in mineral oil afforded significant improvements. Emulsifying as described in Example 1, with the exception of a reduced (1.5 minute) stirring time, expression levels dramatically increased up to 39% (Table 2) of that of the non-emulsified reaction. This emulsion was stable throughout the incubation period, and microscopic visualisation revealed the majority of compartments to have diameters in the range of 2-5 microns (FIG. 2).

TABLE 2

Luciferase activity (in light units (LU)) of luciferase expressed in rabbit reticulocyte extract non-emulsified and emulsified at two different mixing times (3 min and 4 min)

|  | Non emulsified | Emulsified: mixing time | CSR emulsion mix | 1.5% Span80 in mineral oil | 4% Abil |
|---|---|---|---|---|---|
| −DTT | 326789 | 3 min | 945 | 832 | 27828 |
| +DTT | 231318 |  | N.A*. | 1632 | 78970 |
| % activity |  |  | 0.2% | 0.2%/0.6 | 39%/34% |
|  | Background: 249 |  |  |  |  |
| −DTT | 154442 | 4 min | 327 | 338 | 40155 |
| +DTT | 101702 |  | N.A*. | 843 | 29493 |
| % activity |  |  | 0.13% | 0.15%/0.7 | 26%/29% |
|  | Background: 114 |  |  |  |  |

*non-stable emulsion

Example 6

Expression of Human Telomerase in Emulsion Using Novel Oil-Phase

Telomeres are specific DNA structures found at the ends of chromosomes in eukaryotes. They are appended to the 3' end (left after removal of the RNA primer used for DNA replication) by a specialised enzyme telomerase, comprising a RNA component and a protein component. In humans the enzyme comprises human telomeric RNA (hTR) and the human telomerase polypeptide (hTERT) and appends repeated copies of a hexamer repeat (TTAGGG) to the chromosome ends. Telomerase activity has been implicated in both tumor development and progression as well as in senescence and programmed cell death.

Telomerase has so far not been expressed successfully in functional form in prokaryotes, presumably because it requires specialised chaperones (e.g. HSP 90) and accessory factors both for assembly and function. But it can be expressed in eukaryotic cells and also in the rabbit reticulocyte lysate in vitro translation system (Weinrich et al (1997), Nat. Genet., 17, 498-502/Beattie et al (1998, 8, 177-180).

The oil phase from Example 5 was tested for expression of functional human telomerase in RRL. Linear T7-driven templates encoding either wt hTERT and hTR in tandem cloned downstream of the IRES of pCITE4a (Novagen) or hTERT cloned into pCITE4a with hTR cloned separately into a variant of pCITE 4a (in which the IRES was deleted (pCITE-E)) or an inactive deletion mutant of telomerase were prepared by PCR amplification using the respective parental plasmids and primers CITET7ba (5'-GTTTTCCCAGTCACGACGTTG-TAA-3') (SEQ ID NO:1) and CiTEterfo (5'-CCGGATAT-AGTTTTCCTCCTTTCAGC-3') (SEQ ID NO:2).

Expression reactions (50 μl) comprised RRL (80% v/v), telomerase construct (see FIG. 3 legend), methionine (1 mM), telomerase substrate (TS (telomerase substrate) primer (5'-AATCCGTCGAGCAGAGTT-3') (Intergen) 1 μM) (SEQ ID NO:3), PCR enhancer (Promega) (3 μl), dNTPs (25 μl), DTT (20 μM). Emulsions were formed under chilled conditions (on ice) exactly as described above and incubated at 30° C. for 1.5 hours. Emulsions were then extracted with 200 μl chloroform-isoamylalcohol, followed by extraction of aqueous phase with 1 volume phenol-chloroform.

Telomerase reaction products were ethanol precipitated and resuspended in 20 ul sterile water. A PCR-based TRAP (Kim 94) assay (Intergen) was then used to detect telomerase extension products formed in the emulsion Telomerase activity produces a characteristic ladder (with 6 bp spacing for each repeat) (see FIG. 3).

Figure 3:
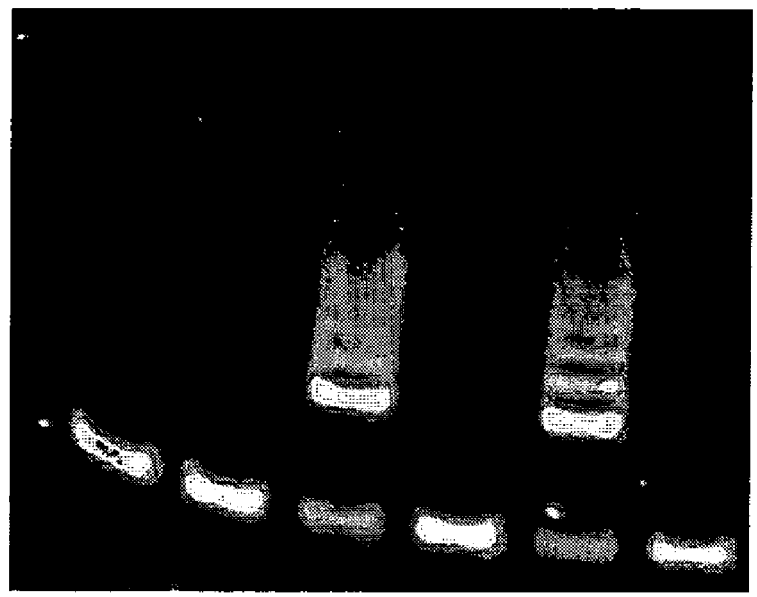
FIG. 3 shows the results of telomerase expression:
Panel A (Non-emulsified): Lane 1, hTERT (75 ng); Lane 2, hTR (75 ng); Lane 3, hTERT+hTR; Lane 4, No construct; Lane 5, Tandem WT expression construct (150 ng) Lane 6, Tandem deletion mutant construct (150 ng)
Panel B: In emulsion, lane annotation same as in panel A.
Figure 3:
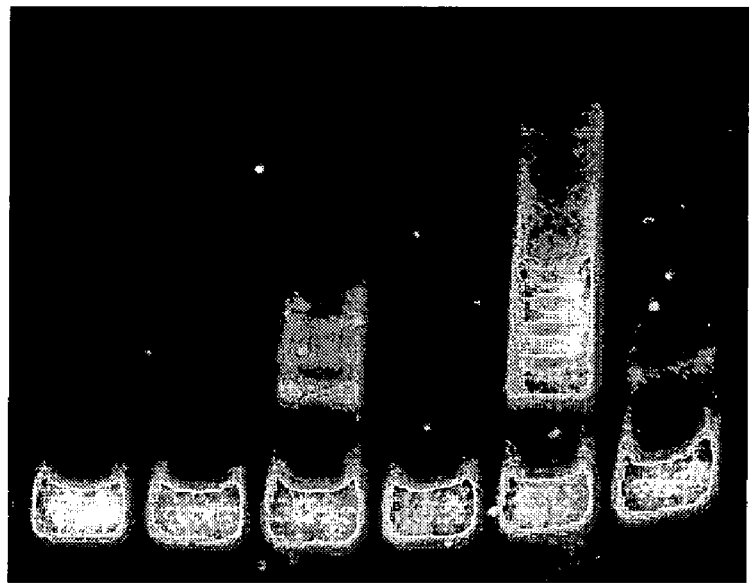

The results indicated expression of functionally active telomerase from the WT template in emulsion. Control experiments either omitting addition of telomerase gene, or using an inactive deletion mutant gave negative results (FIG. 3).

REFERENCES

Anderson, C. W., Straus, J. W. and Dudock, B. S. (1983) Methods Enzymol, 101, 635-44.

Anderson, J. E. (1993) Curr. Op. Struct. Biol., 3, 24-30.

Ash, M. and Ash, I. (1993) Handbook of industrial surfactants. Gower, Aldershot.

Barany, F. (1991) PCR Methods Applic., 1, 5-16.

Becher, P. (1957) Emulsions: theory and practice. Reinhold, New York.

Blattner, F. R. and Dahlberg, J. E. (1972) Nature New Biol, 237, 227-32.

Cahill, P., Foster, K. and Mahan, D. E. (1991) Clin Chem, 37, 1482-5.

Chetverin, A. B. and Spirin, A. S. (1995) Prog Nucleic Acid Res Mol Biol, 51, 225-70.

Cull, M. G., Miller, J. F. and Schatz, P. J. (1992) Proc Natl Acad Sci USA, 89, 1865-9.

Dever T E., Trends Biochem Sci. (1999), 24, 398-403

Dickinson, E. (1994) In Wedlock, D. J. (ed.), Emulsions and droplet size control. Butterworth-Heine-mann, Oxford, Vol. pp. 191-257.

Fahy, E., Kwoh, D. Y. and Gingeras, T. R. (1991) PCR Methods Appl, 1, 25-33.

Fields, S. & Song, O. (1989) A novel genetic system to detect protein-protein interactions. *Nature* 340, 245-6.

Freese, E. (1959) J. Mol. Biol., 1, 87.

Friedberg, E. C., Walker, G. C. and Siede, W. (1995) DNA repair and mutagenesis. ASM Press, Washington D.C.

Ghadessy et al (2001) Proc. Natl. Acad. Sci. USA, 98, 4552-4557

Hermanson, G. T. (1996) Bioconjugate techniques. Academic Press, San Diego.

Hochuli, E., Dobeli, H. and Schacher, A. (1987) J Chromatogr, 411, 177-84.

Hoogenboom, H. R. (1997). Designing and optimizing library selection strategies for generating high-affinity antibodies. *Trends Biotechnol.* 15, 62-70.

Johannsson, A. (1991) In Price, C. P. and Newman, D. J. (ed.), Heterogeneous enzyme immunoassays. Stockton Press, New York, Vol. pp. 295-325.

Johannsson, A. and Bates, D. L. (1988) In Kemeny, D. M. and Challacombe, S. i. (ed.), Amplification by second enzymes. John Wiley, Chichester, Vol. pp. 85-106.

Katanaev, V. L., Kurnasov, O. V. and Spirin, A. S. (1995) Febs Lett, 359, 89-92

Kim, NW & Wu, F (1994), Nucleic Acid Res, 25, 2595-2597

Klug, A. (1995) Ann N Y Acad Sci 758, 143-60.

Klug, A. and Schwabe, J. W. (1995) Faseb T, 9, 597-604.

Kowalczykowski, S. C., Dixon, D. A., Eggleston, A. K., Lauder, S. D. and Rebrauer, W. M. (1994) Microbiol Rev, 58, 401-65.

Landegren, U., Kaiser, R., Sanders, J. and Hood, L. (1988) Science, 241, 1077-80.

Leung, D. W., Chen, E. and Goeddel, D. V. (1989) Technique, 1, 11-15.

Liao, H., McKenzie, T. and Hageman, R. (1986) Proc Natl Acad Sci USA, 83, 576-80.

Lissant, K. J., ed. *Emulsions and emulsion technology*. Surfactant Science New York: Marcel Dekker, 1984.

Low, N. M., Holliger, P. H. and Winter, G. (1996) J Mol Biol, 260, 359-68.

Lowman, H. B., Bass, S. H., Simpson, N. and Wells, J. A. (1991) Biochemistry, 30, 10832-8.

Manley, J. L., Fire, A., Samuels, M. and Sharp, P. A. (1983) Methods Enzymol 101, 568-82.

Mattheakis, L. C., Bhatt, R. R. and Dower, W. J. (1994) Proc Natl Acad Sci USA, 91, 9022-6.

Matts et al (1993), Biochemistry, 32, 7323-7328

Melton, D. A., Krieg, P. A., Rebagliati, M. R., Maniatis, T., Zinn, K. and Green, M. R. (1984) Nucleic Acids Res, 12, 703556.

Miele, E. A., Mills, D. R. and Kramer, F. R. (1983) J Mol Biol, 171, 281-95.

Mize, P. D., Hoke, R. A., Linn, C. P., Reardon, J. E. and Schulte, T. H. (1989) Anal Biochem, 179, 229-35.

Montigiani, S., Neri, G., Neri, P. and Neri, D. (1996) J Mol Biol, 258, 6-13.

Nissim, A., Hoogenboom, H. R. I Tomlinson, I. M., Flynn, G., Midgley, C., Lane, D. and Winter, G. (1994) Embo J, 13, 692-8.

Parmley, S. F. and Smith, G. P. (1988) Gene, 73, 305-18.

Pelham, H. R. and Jackson, R. J. (1976) Eur J Biochem, 67, 247-56.

Pirrung, M. C. and Huang, C. Y. (1996) Bioconjug Chem, 7, 31721.

Roberts, B. E., Gorecki, M., Mulligan, R. C., Danna, K. J., Rozenblatt, S. and Rich, A. (1975) Proc Natl Acad Sci USA, 72, 1922-6.

Roberts, J. W. (1969) Nature, 224, 1168-74.

Roberts, R & Szostak, J. (1997) RNA-peptide fusions for the in vitro selection of peptides and proteins. *Proc Natl Acad Sci USA* 94, 12297-12302.

Rosenberg, M., Weissman, S. and decrombrugghe, B. (1975) J Biol Chem, 250, 4755-64.

Saiki, R. K., Gelfand, D. H., Stoffel, S., Scharf, S. J., Higuchi, R., Horn, G. T., Mullis, K. B. and Erlich, H. A. (1988) Science, 239, 487-91.

Sambrook, J., Fritsch, E. F. and Maniatis, T. (1989) Molecular cloning: a laboratory manual. Cold Spring Harbor Laboratory Press, New York.

Savage, M. D., Mattson, G., Desai, S., Nielander, G. W., Morgensen, S. and Conklin, E. J. (1994) Avidin-biotin chemistry: a handbook. Pierce Chemical Company, Rockford.

Schick, M. J. (1966) Nonionic surfactants. Marcel Dekker, New York.

Sherman, P. (1968) Emulsion science. Academic Press, London.

Smith, G. P. (1985) Science, 228, 1315-7.

Stemmer, W. P. (1994a) Nature, 370, 389-91.

Stemmer, W. P. (1994b) Proc Natl Acad Sci USA, 91, 10747-51.

Stofko, H. R., Carr, D. W. and Scott, J. D. (1992) Febs Lett, 302, 274-8.

Sundberg, S. A., Barrett, R. W., Pirrung, M., Lu, A. L., Kiangsoontra, B. and Holmes, C. P. (1995) J. Am. CheM. Soc., 117, 12050-12057.

Tawfik D. & Griffiths A. D. (1998) *Nature Biotech.* 16, 652

Tripet, B., Yu, L., Bautista, D. L., Wong, W. Y., Irvin, R. T. and Hodges, R. S. (1996) Protein Engng., 9, 1029-1042.

Walker, G. T., Fraiser, M. S., Schram, J. L., Little, M. C., Nadeau, J. G. and Malinowski, D. P. (1992) Nucleic Acids Res, 20, 1691-6.

Weil, P. A., Luse, D. S., Segall, J. and Roeder, R. G. (1979) Cell, 18, 469-84.

Winter, G., Griffiths, A. D., Hawkins, R. E. and Hoogenboom, H. R. (1994) Annu Rev Immunol, 12, 433-55.

Yamagishi, J., Kawashima, H., Matsuo, N., Ohue, M., Yamayoshi, M., Fukui, T., Kotani, H., Furuta, R., Nakano, K. and Yamada, M. (1990) Protein Eng 3, 713-9.

Yelamos, J., Klix, N., Goyenechea, B., Lozano, F., Chui, Y. L., Gonzalez, F. A., Pannell, R., Neuberger, M. S. and Milstein, C. (1995) Nature, 376, 225-9.

Zaccolo, M., Williams, D. M., Brown, D. M. and Gherardi, E. (1996) J Mol Biol, 255, 589-603.

The invention claimed is:

1. An emulsion comprising a surfactant, a hydrophobic phase, a hydrophilic phase, and a plurality of microcapsules containing a functional in vitro eukaryotic expression system, wherein the surfactant is a chemically inert silicone-based surfactant.

2. An emulsion according to claim 1 wherein the silicone-based surfactant is a silicone copolymer.

3. An emulsion according to claim 2 wherein the silicone-based surfactant is polysiloxane-polycetyl-polyethylene glycol copolymer.

4. An emulsion according to claim 1 wherein the surfactant is provided at a v/v concentration in the hydrophobic phase of 4%.

5. An emulsion according to claim 1, wherein the emulsion comprises an in vitro eukaryotic expression system.

6. An emulsion according to claim 1, wherein the eukaryotic expression system comprises all or part of a mammalian cell lysate.

7. An emulsion according to claim 6, wherein the cell lysate is a reticulocyte lysate.

8. An emulsion according to claim 6, wherein the cell lysate is a rabbit reticulocyte lysate.

9. An emulsion according to claim 1, wherein the emulsion is stable during incubation at 30° C. for at least one hour.

10. An emulsion according to claim 1, wherein the hydrophobic phase comprises a mineral oil.

11. The emulsion of claim 1, said microcapsules further comprising genetic elements that are capable of being expressed by said expression system to form a gene product.

12. The emulsion according to claim 11, wherein the expression of a gene product within the emulsion is at a level of at least 1% of that of the gene product achievable by the expression system prior to formation of the emulsion.

13. The emulsion according to claim 12, wherein the expression of the gene product within the emulsion is at a level of at least 10%, at least 20%, or at least 30% of that of the gene product achievable with the expression system prior to formation of the emulsion.

14. A method of forming an emulsion as described in claim 1, comprising agitating together in the presence of a chemically inert silicone-based surfactant a hydrophobic composition and a hydrophilic composition comprising a eukaryotic expression system.

15. A method according to claim 14, wherein the surfactant is present in the hydrophobic composition.

* * * * *

SEQUENCE LISTING

```
<160> NUMBER OF SEQ ID NOS: 3

<210> SEQ ID NO 1
<211> LENGTH: 24
<212> TYPE: DNA
<213> ORGANISM: Artificial
<220> FEATURE:
<223> OTHER INFORMATION: Primer oligonucleotide

<400> SEQUENCE: 1
gttttcccag tcacgacgtt gtaa                                            24

<210> SEQ ID NO 2
<211> LENGTH: 24
<212> TYPE: DNA
<213> ORGANISM: Artificial
<220> FEATURE:
<223> OTHER INFORMATION: Primer oligonucleotide

<400> SEQUENCE: 2
ccggatatag ttcctccttt cagc                                            24

<210> SEQ ID NO 3
<211> LENGTH: 18
<212> TYPE: DNA
<213> ORGANISM: Artificial
<220> FEATURE:
<223> OTHER INFORMATION: Primer oligonucleotide

<400> SEQUENCE: 3
aatccgtcga gcagagtt                                                   18
```